(12) United States Patent
Gradel

(10) Patent No.: US 9,814,603 B2
(45) Date of Patent: Nov. 14, 2017

(54) INSTRUMENTS FOR SETTING ACETABULAR CUP

(76) Inventor: Thomas Gradel, Marignier (FR)

(*) Notice: Subject to any disclaimer, the term of this patent is extended or adjusted under 35 U.S.C. 154(b) by 1426 days.

(21) Appl. No.: 11/576,894

(22) PCT Filed: Oct. 13, 2005

(86) PCT No.: PCT/FR2005/002542
§ 371 (c)(1),
(2), (4) Date: Apr. 9, 2007

(87) PCT Pub. No.: WO2006/040483
PCT Pub. Date: Apr. 20, 2006

(65) Prior Publication Data
US 2008/0077249 A1  Mar. 27, 2008

(30) Foreign Application Priority Data
Oct. 13, 2004 (FR) .................. 04 10879

(51) Int. Cl.
*A61F 2/46* (2006.01)
*A61F 2/34* (2006.01)
(Continued)

(52) U.S. Cl.
CPC .............. *A61F 2/4609* (2013.01); *A61F 2/34* (2013.01); *A61F 2/4637* (2013.01); *A61F 2/4684* (2013.01); *A61F 2/0095* (2013.01); *A61F 2002/30077* (2013.01); *A61F 2002/30354* (2013.01); *A61F 2002/30672* (2013.01); *A61F 2002/3208* (2013.01); *A61F 2002/3404* (2013.01); *A61F 2002/3419* (2013.01);
(Continued)

(58) Field of Classification Search
CPC .. A61F 2/34; A61F 2/4609; A61F 2002/3403; A61F 2002/3438; A61F 2002/4623
USPC .............. 606/91, 99; 623/22.17, 22.19–22.2, 623/22.24–22.29, 22.21, 23.43
See application file for complete search history.

(56) References Cited

U.S. PATENT DOCUMENTS 4,632,111 A 12/1986 Roche
5,169,399 A * 12/1992 Ryland et al. .................. 606/91
(Continued)

FOREIGN PATENT DOCUMENTS

DE 19628193 A1 1/1998
EP 0504521 A1 9/1992
(Continued)

*Primary Examiner* — Bruce E Snow
*Assistant Examiner* — Melissa Hoban
(74) *Attorney, Agent, or Firm* — William H. Eilberg

(57) ABSTRACT

A cup and a temporary insert are respectively configured to be tightly press fitted into each other along their periphery. The temporary insert includes a through hole communicating outside with a free space between the outer surface of the temporary insert and the inner surface of the cup. In the through hole can be engaged the threaded end of an impactor, for manipulating the cup when it is being set. A syringe can be engaged, enabling a liquid under pressure to be injected into the free space, thus separating the temporary insert from the cup without any risk of damaging the inner surface of the cup. Thus, the cup can be securely manipulated when it is being set without any risk of damaging the inner surface of the cup.

2 Claims, 4 Drawing Sheets

(51) Int. Cl.
*A61F 2/00* (2006.01)
*A61F 2/30* (2006.01)
*A61F 2/32* (2006.01)

(52) U.S. Cl.
CPC .......... *A61F 2002/4624* (2013.01); *A61F 2002/4629* (2013.01); *A61F 2002/4641* (2013.01); *A61F 2002/4653* (2013.01); *A61F 2002/4681* (2013.01); *A61F 2002/4693* (2013.01); *A61F 2210/0066* (2013.01); *A61F 2220/0033* (2013.01)

(56) References Cited

U.S. PATENT DOCUMENTS

| | | | | |
|---|---|---|---|---|
| 5,320,625 | A | * | 6/1994 | Bertin ............... 606/91 |
| 5,474,560 | A | * | 12/1995 | Rohr, Jr. ............ 606/91 |
| 5,904,688 | A | * | 5/1999 | Gilbert et al. ....... 606/86 R |
| 5,928,287 | A | * | 7/1999 | Keller .............. 623/22.21 |
| 5,938,701 | A | * | 8/1999 | Hiernard et al. ...... 606/99 |
| 5,954,727 | A | * | 9/1999 | Collazo ............. 606/91 |
| 6,027,505 | A | * | 2/2000 | Peter et al. ......... 606/91 |
| 6,152,930 | A | * | 11/2000 | Mastrorio ........... 606/99 |
| 6,468,281 | B1 | * | 10/2002 | Badorf et al. ....... 606/91 |
| 2003/0229357 | A1 | * | 12/2003 | Dye ................ 606/99 |
| 2004/0172039 | A1 | * | 9/2004 | Dye ................ 606/99 |
| 2005/0203535 | A1 | * | 9/2005 | Parry et al. ........ 606/91 |

FOREIGN PATENT DOCUMENTS

| | | | | |
|---|---|---|---|---|
| FR | 2785523 | A1 | | 5/2000 |
| FR | 2809305 | A1 | | 11/2001 |
| GB | 2423715 | A | * | 9/2006 ............. A61F 2/46 |

\* cited by examiner

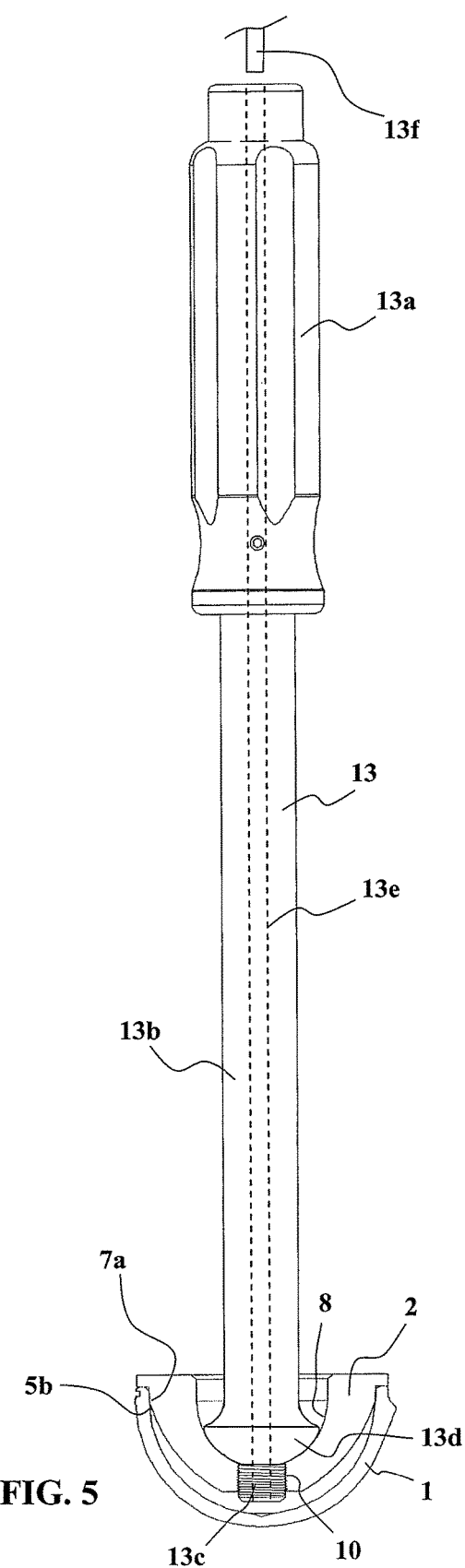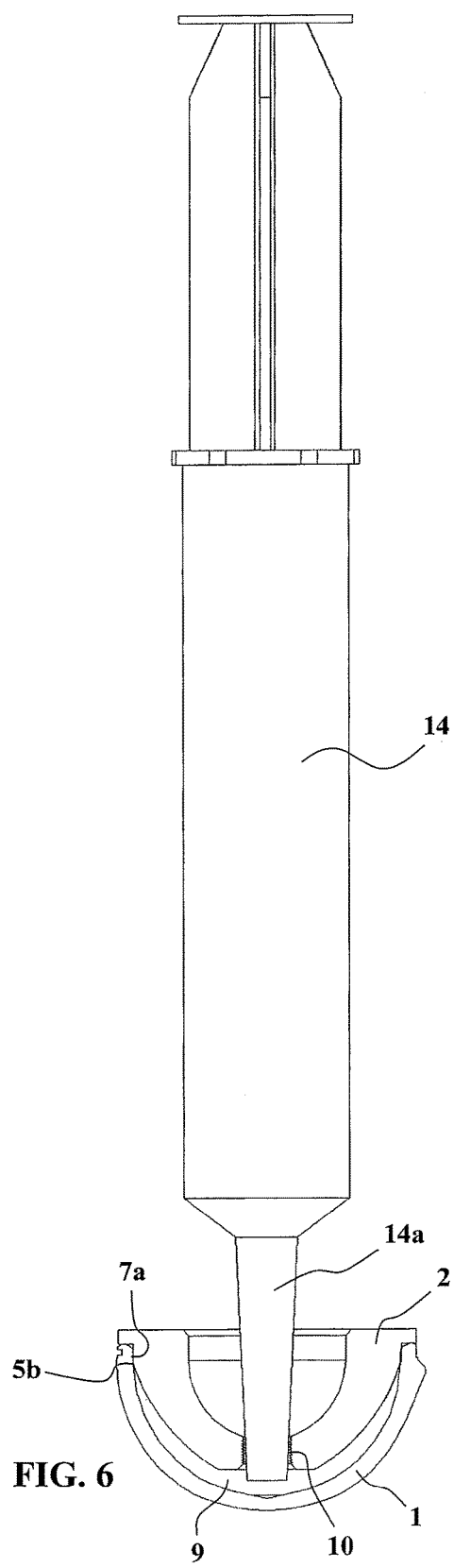

INSTRUMENTS FOR SETTING ACETABULAR CUP

TECHNICAL FIELD OF THE INVENTION

The present invention concerns instruments for setting a prosthesic acetabular cup intended to replace the natural acetabular cup of the hip.

A total hip prosthesis comprises two parts constituting a ball-joint, namely a female part intended to replace the natural acetabular cup of the hip and a male part intended to replace the head of the femur.

The male part of the joint generally includes a rod intended to penetrate into the medullary canal of the femur and the proximal end whereof is connected by a neck to a spherical head intended to penetrate into the acetabular cup.

The female part of the joint, which has to replace the natural acetabular cup of the hip, and will be generally referred to as the acetabular cup, usually comprises a hemispherical metallic cup with a convex proximal face and a concave distal face, the convex proximal face being accommodated in a prepared acetabular cavity in the pelvic bone, the concave distal face receiving the hemispherical convex proximal face of an insert made from a plastic material with a low coefficient of friction such as polyethylene or a ceramic, the insert itself having a coaxial hemispherical distal cavity that receives the spherical head of the male part of the joint.

Single mobility prostheses have already been provided, in which the polyethylene or ceramic insert is fixed in the concave distal face of the metallic cup, the rotation movements of the joint occurring between the spherical head of the male part of the prosthesis and the hemispherical distal cavity of the insert.

Dual mobility prostheses have also been proposed already, in which the polyethylene or ceramic insert itself has some capacity for rotation in the concave distal face of the metallic cup, so that the rotation movements of the joint occur on the one hand between the convex proximal face of the insert and the concave distal face of the metallic cup and on the other hand between the hemispherical distal cavity of the insert and the spherical head of the male joint part.

In all cases, one problem is positioning and fixing the metallic cup in the acetabular cavity in the bone. The quality of fitting and fixing the cup into the acetabular cavity is in fact essential for the longevity of the prosthesis, i.e. for the durability of the connection between the bone and the metallic cup.

Accordingly, when setting the cup in the acetabular cavity, it must be possible to use an impactor to apply a force to drive the cup into the acetabular cavity in the bone, to apply rotation torques for adjusting the orientation of the cup, and in particular to hold the cup in a fixed position long enough for a cement to set between the convex proximal face of the cup and the acetabular cavity in the bone. It must then be possible to withdraw the impactor without applying force to the cup, in order not to degrade the quality of its fixing into the acetabular cavity.

However, and especially in the case of dual mobility prostheses in which the concave distal face of the cup constitutes a sliding surface that must be perfectly smooth, and which for this purpose generally receives a mirror polish, for the insert to be able to pivot freely in the cup, it is necessary to prevent all risk of deterioration of this concave distal face of the cup by the instruments for setting the cup into the acetabular cavity. For example, an instrument able to expand and contract radially and bearing on a plurality of discontinuous areas of the concave distal face of the cup to hold the cup during setting would necessarily cause permanent and localized deformation of the concave distal face of the cup or insufficient retention, and so this way of holding it is not acceptable.

The document EP 0 504 521 A1 teaches the provision of an impactor having a convex proximal face that clips into the concave distal face of the cup. After fixing the cup into the acetabular cavity, the impactor is separated from the cup by means of a sliding axial bar that bears axially on the center of the convex distal sliding face of the cup and is set in motion by means of a trigger operated by the surgeon. The bearing engagement of the sliding bar locally degrades the sliding face of the cup, which is not acceptable.

The document FR 2 809 305 A1 teaches holding a cup onto a head at the end of an impactor by creating a vacuum in a free space left between the head and the concave distal face of the cup. For this purpose the impactor body is provided with a manually operated piston pump that is used to aspirate air from the free space via a hole passing through the head. An O-ring opposes entry of air into the free space. The percussive force is applied by the head to the concave distal face portion of the cup around the free space. The device is complex, necessitating assembly of many parts, with a plurality of gas sealing means, and the document does not mention or solve the problem of deformation of the concave distal face of the cup as a result of unequal bearing stresses.

Various other means for holding the cup without bearing on its concave distal face have been envisaged. A first such means consists in holding the cup by its circular lip and by the adjacent portion of its external surface. However, this locally degrades the bone in the retaining area around the cup, which weakens the subsequent retention of the cup in the bone.

The document U.S. Pat. No. 4,632,111 A describes means adapted to be used for fixing an undercut cup. The impactor comprises a hemispherical head mounted at the end of a handle and engaging in the concave distal face of the cup. An annular flange is mounted to slide on the handle and is pushed toward the head by a bush screwed onto the handle. An elastomer ring is compressed axially between the head and the flange and expands radially, thus coming to bear against an annular undercut portion of the concave distal face of the cup to fix the impactor. The bush is unscrewed to withdraw the flange, to retract the elastomer ring and then to withdraw the impactor. This device is complex, consisting of an assembly of a relatively large number of parts, and is not suited to fixing cups that are not undercut. Moreover, the screwing maneuver induces unwanted torques on the cup, with the risk of degrading the quality of its fixing into the acetabular cavity.

The document DE 196 28 193 A describes an impactor head with a peripheral O-ring and a centering tenon engaging in a hole passing through the bottom of the cup. This pierced cup structure is not applicable to a dual mobility prosthesis.

Thus the cup setting instruments known at present do not provide satisfactory retention of the cup for free orientation thereof and sufficient bearing engagement thereof in the bone without degrading the cup or the adjacent bone.

After setting the cup in the acetabular cavity, the surgeon generally needs to fit a trial insert into the cup, this insert having substantially the same shape as the permanent insert of the prosthesis, and being intended to receive the male part of the joint one or more times. This enables the surgeon to try out several sizes of the male part of the joint and to carry out mobility tests. The aim is to enable the surgeon to choose the most appropriate size of the male part of the joint, as a function of the morphology of the patient. He then removes the trial insert to fit the permanent insert in which the head of the chosen male part of the joint will be accommodated.

For these operations, using the devices described in the documents referred to hereinabove, the surgeon must therefore have available a relatively large number of parts to be assembled, each part having to be sterile: an acetabular cup prosthesis, a trial insert, a permanent insert, a plurality of prosthesis male parts, and complex instruments for holding the cup while setting it. In particular, none of the above documents describes or imparts to the impactor head a trial insert function such that the trial insert is able to receive a femoral head.

Given that patients come in diverse sizes, the surgeon must necessarily have a relatively large stock of parts, which increases the overall amount tied up in this way.

STATEMENT OF THE INVENTION

The problem addressed by the present invention is to avoid the drawbacks of known acetabular cup prosthesis setting instruments by proposing a new instrument structure that combines mechanically strong retention of the cup on an impactor for manipulating the cup and setting it in an acetabular cavity and total absence of deformation or deterioration of the concave distal face of the cup by the instruments.

With the means according to the invention, it must be possible to impact the cup into the acetabular cavity, orient it in a precise and satisfactory way and fix it correctly into the acetabular cavity, without degrading the concave distal sliding surface of the cup and without any excrescence on the external surface of the cup or deterioration of the peripheral area of bone around the cup.

The means according to the invention must be applicable without distinction to single mobility prostheses and dual mobility prostheses.

Another object of the invention is to reduce the number of sterile parts that the surgeon must assemble when setting a prosthesis. Thus the stocks of instruments can be reduced and the work of the surgeon facilitated, whilst reducing the risks associated with the operation.

According to another object of the invention, to guarantee a high quality of the fixing of the cup into the bone, it must be possible to separate the instruments from the cup without applying to the cup a mechanical force tending to move it in translation or rotation relative to the bone into which it is fixed.

To achieve the above and other objects, the invention proposes a set of acetabular cup prosthesis setting means, comprising a cup delimited by a convex proximal face, a concave distal face with a sliding surface, and a peripheral lip, and further comprising an adapter for fastening the cup to an impactor, the adapter including:

fixing means for detachably fixing the adapter to the impactor, fixing means on the cup, leaving a free space between the adapter and the cup once the adapter is fixed to the cup, an access hole through which the free space between the adapter and the cup communicates with the outside, wherein:

the cup comprises, on its concave distal face, a cylindrical or slightly conical annular retaining surface extending the sliding surface toward the peripheral lip, the adapter comprises a cylindrical or slightly conical annular engagement surface the same shape as the annular retaining surface of the cup, with the result that the adapter may be forcibly retained in fluid-tight manner with its annular engagement surface gripped radially in the annular retaining surface of the cup.

Because the adapter is conformed to be forcibly retained in fluid-tight manner in the cup around its periphery, it bears only on the annular retaining surface of the concave distal face of the cup, away from the sliding surface, avoiding the production of any irregularity on the sliding surface of the cup.

Moreover, because a free space remains between the adapter and the cup once the adapter is forcibly retained in the cup in fluid-tight manner by its annular engagement surface, and because the adapter includes an access hole, the adapter may subsequently be withdrawn from the cup by injecting a fluid under pressure, advantageously a liquid under pressure, through the access hole into the free space between the adapter and the cup. The fluid under pressure produces a symmetrical resultant axial force that ejects the adapter from the cup and applies to the sliding surface of the cup a mechanical stress that is regularly distributed because it is a fluid pressure. This again avoids any localized deformation of the sliding surface of the cup and prevents the application of any traction, oscillation or rotation stress to the cup.

The forcible immobilization of the adapter in the cup may be sufficient to ensure strong fastening of the adapter and thus strong fastening of the cup onto the impactor.

Further providing abutment means on the adapter intended to bear axially on the peripheral lip of the cup to limit the penetration of the adapter into the cup may nevertheless be preferred. The impactor can then apply a higher impacting force to the adapter, which force is transmitted to the cup on the one hand by the annular surface of the adapter engaged in the cup and on the other hand by the abutment means bearing on the peripheral lip of the cup.

Improved fastening of the cup to the adapter may advantageously be obtained by providing for the annular retaining surface of the cup to comprise at least one annular groove and for the annular engagement surface of the adapter to comprise at least one corresponding annular rib adapted to be engaged in the annular groove. The depth of the groove and the rib is made relatively small to improve the fastening, but without compromising subsequent separation of the adapter from the cup.

The cup may preferably comprise a substantially hemispherical sliding surface that is advantageously mirror polished, extended by a short cylindrical or slightly conical annular retaining surface. The adapter is then able to bear on the annular retaining surface, which is not a sliding surface of the cup, which reduces the mechanical stresses applied to the hemispherical sliding surface.

The adapter may be fastened to the impactor by any means. However, means for fixing the adapter to the impactor may be preferred that comprise a threaded fixing hole in the adapter for screwing in a corresponding threaded portion of the impactor. If the fixing hole is not the access hole, it must be a blind hole.

The adapter according to the invention is used as connecting means between the impactor and the cup.

However, the adapter may advantageously have a second function, namely a temporary trial insert function, by providing an adapter that comprises, on its distal face, a hemispherical cavity dimensioned to enable the engagement of the head of a femoral prosthesis. The hemispherical cavity may be concentric with the convex proximal face of the adapter, especially in the case of dual mobility prostheses. Clearly this reduces the number of parts to be assembled by the surgeon to set the prosthesis, since there is no longer any need for a specific trial insert separate from the adapter.

The access hole to the free space between the cup and the adapter is advantageously conformed and dimensioned for the fluid-tight engagement therein of the end of a syringe. In this way, fluid under pressure can be injected by means of a simple syringe, an instrument that is generally available to the surgeon, without necessitating further equipment.

The access hole of the adapter may preferably be threaded to fulfill simultaneously the adapter fixing hole function by enabling a corresponding threaded portion of the impactor to be screwed into the adapter.

The access hole of the adapter may then advantageously be located in the bottom of a hemispherical cavity dimensioned to allow the engagement of the head of a femoral prosthesis.

As in the known prostheses, the trial insert type adapter may be made of polyethylene. On the other hand, the permanent insert may be made of polyethylene or ceramic.

There is further provided an impactor having a threaded portion for screwing it into a threaded fixing hole in the adapter.

The impactor may preferably further include, at the base of the threaded portion, a hemispherical portion conformed and dimensioned to be accommodated in a corresponding hemispherical cavity of the adapter. This provides a more regular distribution of mechanical stresses between the impactor and the adapter, which stresses are relatively high and occur on impacting the cup into the acetabular cavity.

According to the invention, there may advantageously be supplied to the surgeon a temporary trial insert type adapter with its engagement annular surface previously forcibly immobilized in fluid-tight manner in the annular retaining surface of the cup, this assembly advantageously being sterile and packaged in a sealed protective envelope.

At the time of assembling the adapter and the cup, which assembly may be carried out at the production factory, the following succession of steps may advantageously be used:
 a) cooling the adapter to reduce its dimensions,
 b) positioning the adapter in the cup,
 c) allowing the adapter, once in place in the cup, to return to room temperature to expand it so that the annular engagement surface of the adapter is forcibly immobilized in fluid-tight manner in the annular retaining surface of the cup.

There is preferably further provided a step of sterilizing the adapter and the cup by means of gamma rays once they have been fastened together.

After setting the cup, the adapter may be separated from the cup by a step during which a fluid under pressure, advantageously a liquid under pressure, is injected through the access hole into the free space between the adapter and the cup.

BRIEF DESCRIPTION OF THE DRAWINGS

Other objects, features and advantages of the present invention will emerge form the following description of particular embodiments, given with reference to the appended drawings, in which:

FIG. 5 is a side view in section showing an impactor engaged in the temporary insert of the insert-cup assembly from FIG. 4; and FIG. 6 is a side view in section showing a syringe engaged in the passage of the temporary insert in an insert-cup assembly according to the invention.

DESCRIPTION OF THE PREFERRED EMBODIMENTS

In the embodiment shown in FIGS. 1 to 4, the acetabular cup prosthesis setting instruments comprise a cup 1 and an adapter 2 conformed as an impaction and temporary trial insert.

The cup 1 constitutes the permanent cup intended to be fixed into an acetabular cavity in the pelvic bone.

On the other hand, the adapter 2 has at least the function of an intermediate part between the cup 1 and an impactor that is used to manipulate the cup 1 when setting it in the acetabular cavity, and the adapter 2 is intended then to be replaced by a permanent insert.

Figure 4:
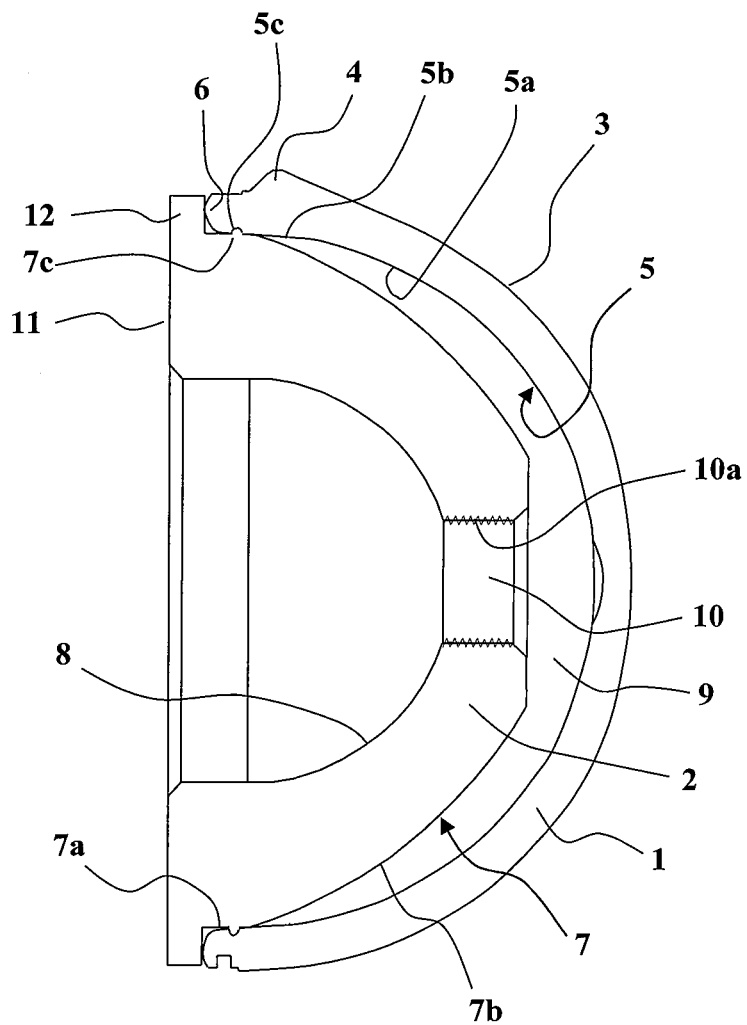
FIG. 4 is a side view in diametral section taken along the line A-A in FIG. 3.

The cup 1 is a hemisphere with a relatively thin wall, having a convex proximal face 3, seen better in FIG. 4, of generally hemispherical shape, optionally with anchoring fins 4, and a concave distal face 5 comprising a hemispherical sliding surface 5a extended by a cylindrical or slightly conical annular retaining surface 5b extending to a peripheral lip 6.

The hemispherical surface 5a of the cup 1 is perfectly smooth and regular, preferably mirror polished, in order to constitute a sliding surface in which a hemispherical permanent insert subsequently introduced into the cup 1 after it is fitted in the acetabular cavity can pivot perfectly.

The adapter 2 has a generally rounded shape delimited by a convex proximal face 7 and a distal face 11 with a hemispherical cavity 8.

The convex proximal face 7 of the adapter 2 has a cylindrical or slightly conical annular engagement surface 7a and a central dome 7b set back from the hemispherical shape consisting of the hemispherical sliding surface 5a of the cup 1. As a result of this, in the force-fitted position shown in FIG. 4, there remains a free space 9 between the temporary insert 2 and the cup 1.

The annular engagement surface 7a has a shape that corresponds to that of the annular retaining surface 5b and a diameter such that it is forcibly retained in the annular retaining surface 5b of the cup 1, so that the adapter 2 and the cup 1 are able to constitute a subassembly able to withstand, without relative movement with respect to each other, high mechanical stresses, greater than the forces that must be applied to a cup when setting it in the acetabular cavity.

In FIGS. 5 and 6, the annular engagement surface 7a and the annular retaining surface 5b are smooth.

Alternatively, in the FIG. 4 embodiment, the annular retaining surface 5b of the cup 1 comprises at least one annular groove 5c and the annular engagement surface 7a of the adapter 2 comprises at least one corresponding annular rib 7c adapted to be engaged in the annular groove 5c.

The hemispherical cavity 8 of the adapter 2 is dimensioned to receive a ball-joint head of a femoral joint male part. The adapter 2 can therefore constitute a temporary trial insert.

At the bottom of the adapter 2 is an access hole 10 through which the free space 9 between the adapter 2 and the cup 1 communicates with the outside.

The distal face 11 of the adapter 2 is flanked by a circular peripheral rib 12 that constitutes abutment means bearing on the peripheral lip 6 of the cup 1 in the force-fitted position shown in FIG. 4. As a result of this, the peripheral rib 12 opposes further penetration of the adapter 2 into the cup 1. In the embodiment shown in the figures, the access hole 10 also constitutes means for detachably fixing an impactor. For this purpose it includes an internal thread 10*a*.

Consider now FIG. 5, which shows again the cup 1, the temporary trial insert type adapter 2, the hemispherical cavity 8 of the adapter 2, and the threaded access hole 10.

This figure also shows an impactor 13 comprising a handle 13*a*, a stem 13*b* and a threaded end 13*c* that is screwed into the threaded access hole 10. The impactor 13 preferably includes, at the base of the threaded portion 13*c*, a hemispherical portion 13*d* conformed and dimensioned to be accommodated in the corresponding hemispherical cavity 8 of the adapter 2. Thus, the impactor 13 is used to manipulate the cup 1 during its insertion into and positioning in the acetabular cavity.

FIG. 6 shows a step of separation of the adapter 2 from the cup 1. In this embodiment, a syringe 14 is provided containing an appropriate liquid, for example physiological serum, and having an end-piece 14*a* that is engaged in fluid-tight manner in the access hole 10 of the adapter 2. The syringe 14 is then used to inject a liquid under pressure into the free space 9, causing separation of the adapter 2 from the cup 1.

Alternatively, to avoid the use of a supplementary syringe, the impactor 13 may comprise a tubular handle: thus FIG. 5 shows an impactor 13 including an axial passage 13*e*. During the separation step, liquid may be introduced into the axial passage 13*e* and then a piston-rod 13*f* that forces the liquid into the free space 9.

In the embodiment shown in the figures, the adapter 2 includes the hemispherical cavity 8, to fulfill the temporary trial insert function. Nevertheless, without departing from the scope of the invention, the adapter 2 could have no such hemispherical cavity, serving only as an adapter for positioning the cup 1 in the acetabular cavity by means of the impactor 13.

Likewise, in the embodiment shown, the access hole 10 simultaneously serves as means for fixing the impactor 13 to the adapter 2. Alternatively, a hole could be provided in the central portion of the adapter 2 for fixing the impactor 13, whereas the access hole 10 for injecting fluid could be moved. The hole for fixing the impactor must be a blind hole in this case.

The use of the instruments according to the invention is explained hereinafter.

In the factory, the adapter 2 may be assembled into the cup 1 by a procedure comprising the following steps:

a) the adapter 2 is cooled to a sufficiently low temperature to reduce its dimensions slightly, said dimensions being initially such that the diameter of the annular engagement surface 7*a* of the adapter 2 is slightly greater than the diameter of the annular retaining surface 5*b* of the cup 1 at the same temperature; lowering the temperature of the adapter 2 reduces its outside diameter, in order to facilitate its engagement with the entry of the cup 1, which itself remains at room temperature;

b) the adapter 2 is then positioned in the cup 1, so that the peripheral rib 12 abuts against the peripheral lip 6;

c) once in place in the cup 1, the adapter 2 is allowed to return to room temperature to expand it, so that the adapter 2 is force-fitted into and forcibly retained in fluid-tight manner in the cup 1 by its annular engagement surface 7*a*.

Figure 1:
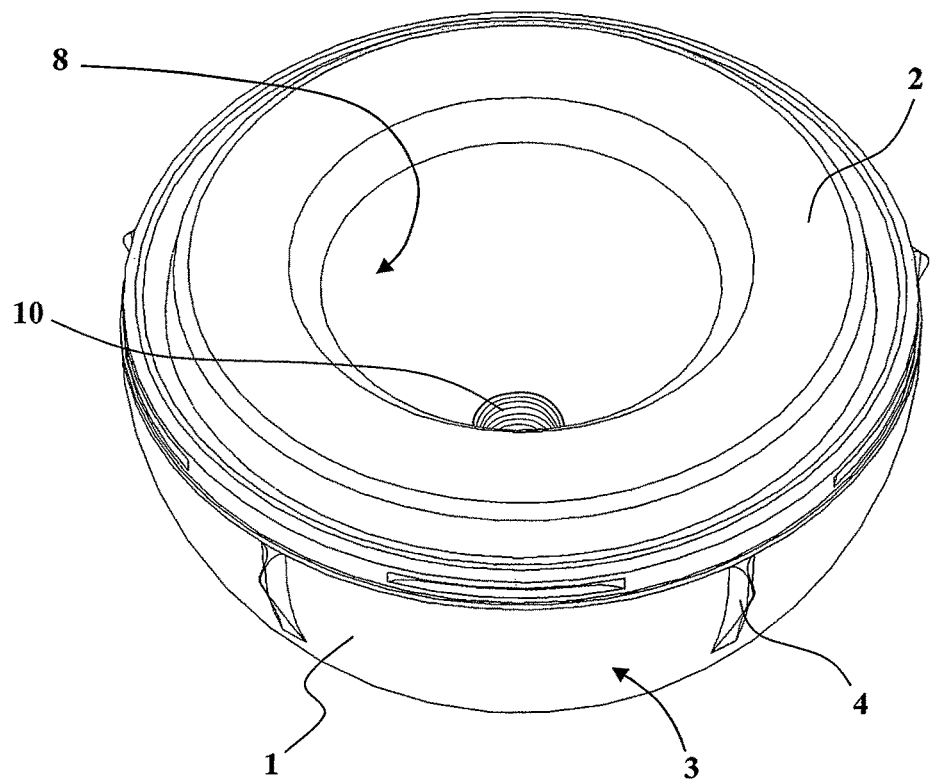
FIG. 1 is a perspective view of an assembly according to one embodiment of the invention comprising an acetabular cup prosthesis in which is forcibly engaged an impaction and temporary trial insert type adapter.
Figure 2:
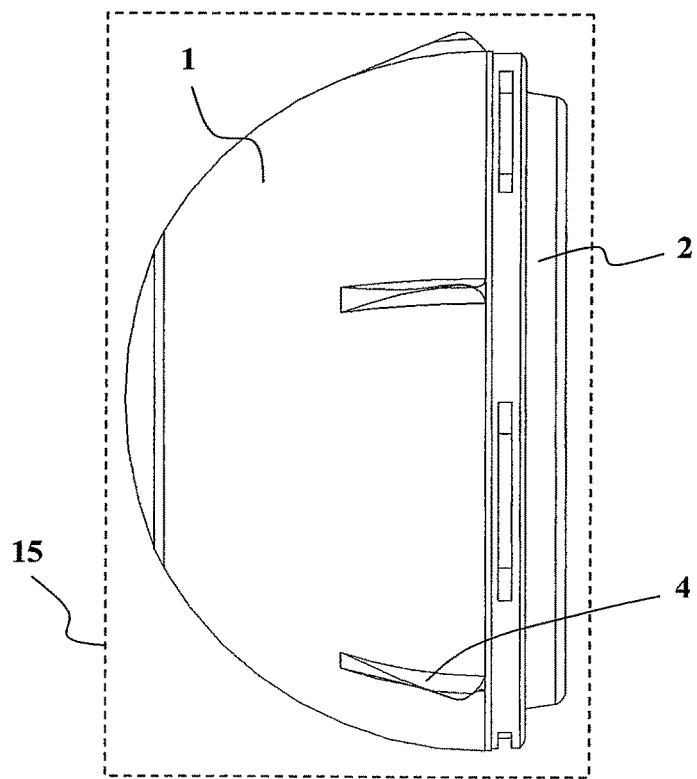
FIG. 2 is a side view of the assembly from FIG. 1, inserted into a sealed protective envelope.
Figure 3:
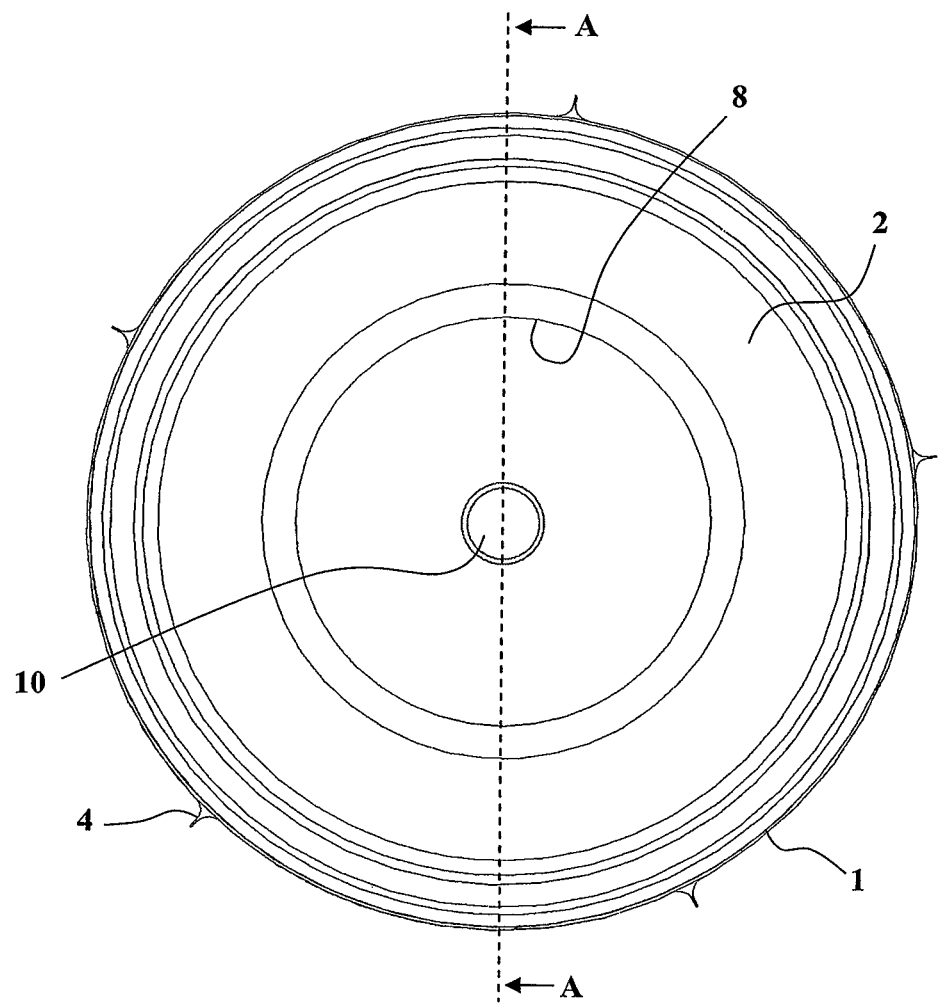
FIG. 3 is a front view of the assembly from FIG. 1.

The adapter-cup assembly is then sterilized by gamma rays in a sealed protective envelope 15 (FIG. 2). From this moment onwards the adapter-cup assembly is packaged in the sterile state in the sealed protective envelope 15.

At the place of use, i.e. in the operating theatre, the surgeon removes the sealed protective envelope 15 and can screw a sterile impactor 13 into the access hole 10. The surgeon can then manipulate the cup 1 by means of the impactor 13 and the force-fitted adapter 2, imparting to the cup 1 all of the mechanical forces necessary for positioning it and orienting it.

The surgeon then removes the impactor 13 by unscrewing it.

The surgeon can then fit into the hemispherical cavity 8 of the adapter 2 a ball-joint head of the temporary insert type, which then serves as the temporary trial insert.

Once the prosthesis male part has been chosen, the surgeon can remove the temporary insert 2 from the cup 1 by introducing a liquid or other fluid under pressure, by means of a syringe 14 as shown in FIG. 6, or into the impactor 13 with the piston-rod 13*f* and the axial passage 13*e*, as shown in FIG. 5.

He then fits a permanent insert into the cup 1 which is itself in place in an acetabular cavity.

All the above operations are carried out with no risk of deformation of the hemispherical sliding surface 8 of the cup 1 and with no unwanted forces on the cup 1.

The present invention is not limited to the embodiments that have been explicitly described, and encompasses variants and generalizations thereof within the scope of the following claims.

The invention claimed is:

1. Set of acetabular cup prosthesis setting means, comprising a cup delimited by a convex proximal face, a concave distal face defining an interior surface of the cup, and a peripheral lip, and further comprising an adapter for fastening the cup to an impactor, the adapter including:
   fixing means for detachably fixing the adapter to the impactor,
   fixing means on the cup, leaving a free space between the adapter and the cup once the adapter is fixed to the cup,
   an access hole through which the free space between the adapter and the cup communicates with the outside,
   wherein:
   the cup comprises a cylindrical or slightly conical annular retaining surface extending the concave distal face toward the peripheral lip, wherein the concave distal face is free of holes,
   the adapter comprises a continuous cylindrical or slightly conical annular engagement surface permanently having a same shape as the annular retaining surface of the cup, wherein the retaining surface of the cup, and the engagement surface of the adapter, are both cylindrical or slightly conical,
   wherein the adapter and the cup are in contact, continuously along said annular engagement surface, and in a vicinity of the peripheral lip of the cup, wherein the engagement surface of the adapter engages the interior surface of the cup, and wherein the engagement surface of the adapter has a diameter, at room temperature, which is slightly greater than a diameter of the retaining surface of the cup, wherein the adapter is forcibly retained in a fluid-tight manner by its annular engagement surface being gripped radially in the annular retaining surface of the cup while the free space between the adapter and the cup communicates with the outside.

2. Set of acetabular cup prosthesis setting means, comprising a cup delimited by a convex proximal face, a concave distal face defining an interior surface of the cup, and a peripheral lip, and further comprising an adapter for fastening the cup to an impactor, the adapter including:

fixing means for detachably fixing the adapter to the impactor, fixing means on the cup, leaving a free space between the adapter and the cup once the adapter is fixed to the cup, an access hole through which the free space between the adapter and the cup communicates with the outside, wherein:

the cup comprises a cylindrical or slightly conical annular retaining surface extending the concave distal face toward the peripheral lip, wherein the concave distal face is free of holes, the adapter comprises a continuous cylindrical or slightly conical annular engagement surface permanently having a same shape as the annular retaining surface of the cup, wherein the retaining surface of the cup, and the engagement surface of the adapter, are both cylindrical or slightly conical, wherein the adapter and the cup are in contact, continuously along said annular engagement surface, and only in a vicinity of the peripheral lip of the cup, wherein the engagement surface of the adapter engages the interior surface of the cup, and wherein the engagement surface of the adapter has a diameter, at room temperature, which is slightly greater than a diameter of the retaining surface of the cup, wherein the adapter is forcibly retained in a fluid-tight manner by its annular engagement surface being gripped radially in the annular retaining surface of the cup while the free space between the adapter and the cup communicates with the outside.

* * * * *